United States Patent [19]
Lynch et al.

[11] Patent Number: 5,922,906
[45] Date of Patent: Jul. 13, 1999

[54] SIDE CHAINS SYNTHESIS FOR AN ANTHIARRHYTHMIC COMPOUND

[75] Inventors: Joseph E. Lynch, Plainfield; Yao-Jun Shi, Edison; Kenneth M. Wells, Neshanic Station, all of N.J.

[73] Assignee: Merck & Company, Inc., Rahway, N.J.

[21] Appl. No.: 09/128,141

[22] Filed: Aug. 3, 1998

Related U.S. Application Data

[60] Provisional application No. 60/058,060, Sep. 5, 1997.

[51] Int. Cl.$^6$ .................................................. C07B 37/06
[52] U.S. Cl. ............................................................ 562/479
[58] Field of Search .............................................. 562/479

[56] References Cited

U.S. PATENT DOCUMENTS 5,426,185  6/1995  Baldwin et al. ........................ 540/509

*Primary Examiner*—Samuel Barts
*Attorney, Agent, or Firm*—Valerie J. Camara; Mark R. Daniel

[57] ABSTRACT

The present invention is directed to an improved process for preparing the phenylacetic acid side chain of the compound of the formula

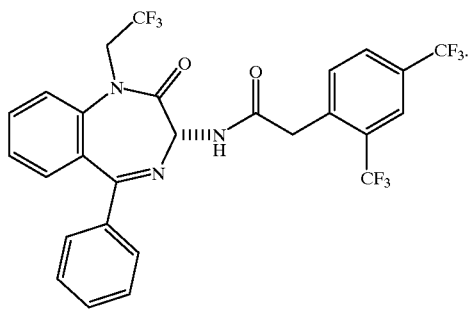

This compound exhibits utility as a Class III antiarrhythmic agent.

4 Claims, No Drawings

SIDE CHAINS SYNTHESIS FOR AN ANTHIARRHYTHMIC COMPOUND

This application was filed from provisional application 60/058,060 filed Sep. 5, 1997.

BACKGROUND OF THE INVENTION

This invention relates to a process for preparing the side chain of a Class III antiarrhythmic compound of the kind disclosed in U.S. Pat. No. 5,426,185. The previous method to prepare the side chain relied on a −78° C. metalation reaction that would be difficult and expensive to use on a commercial scale. This process employs a novel aromatic nitro group displacement to generate a key intermediate in the synthesis of the side chain.

Arrhythmias often occur as complications to cardiac diseases such as myocardial infarction and heart failure. In a serious case, arrhythmias give rise to a ventricular fibrillation and can cause sudden death.

Though various antiarrhythmic agents are now available on the market, agents which exhibit both satisfactory effects and high safety profiles have not been marketed. For example, antiarrhythmic agents of Class I, according to the classification of Vaughan-Williams, which cause a selective inhibition of the maximum velocity of the upstroke of the action potential (Vmax) are inadequate for preventing ventricular fibrillation. In addition, they have problems regarding safety, namely, they cause a depression of the myocardial contractility and have a tendency to induce arrhythmias due to an inhibition of the impulse conduction. Beta-adrenoceptor blockers and calcium antagonists which belong to Class II and IV respectively, have a defect in that their effects are either limited to a certain type of arrhythmia or are contraindicated because of their cardiac depressant properties in certain patients with cardiovascular disease. Their safety, however, is higher than that of the antiarrhythmic agents of Class I.

Antiarrhythmic agents of Class III are drugs which cause a selective prolongation of the duration of the action potential without a significant depression of the Vmax. Drugs in this class are limited. Examples such as sotalol and amiodarone have been shown to possess Class III properties. Sotalol also possesses Class II effects which may cause cardiac depression and be contraindicated in certain susceptible patients. Also, amiodarone is severely limited by side effects. Drugs of this class are expected to be effective in preventing ventricular fibrillations. Pure Class III agents, by definition, are not considered to cause myocardial depression or an induction of arrhythmias due to the inhibition of the action potential conduction as seen with Class I antiarrhythmic agents.

SUMMARY OF THE INVENTION

There is disclosed a novel process for preparing the phenylacetic acid side chain for the compound of the formula

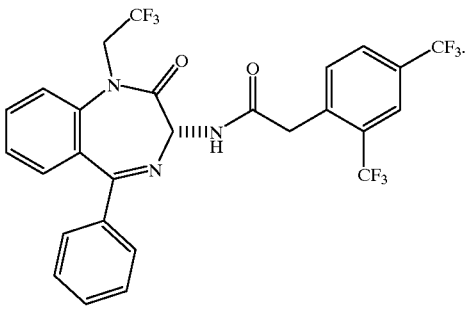

This compound has been found to show utility as a Class III antiarrhythmic agents.

DETAILED DESCRIPTION OF THE INVENTION

The present invention is directed to a novel four-step process for preparing the side chain for Compound 1 through the displacement of an aromatic nitro group with dimethyl malonate. The previous process relied on a a −78° C. metalation reaction that due to the extremely low temperaure requirement, would be difficult to employ on a commercial scale.

Throughout the specification and appended claims, a given chemical formula or name shall encompass all optical and stereoisomers as well as racemic mixtures where such isomers and mixtures exist.

The term alkyl refers to straight, branched or cyclic chain hydrocarbon groups, e.g., methyl, ethyl, n-propyl, isopropyl, n-butyl, pentyl, hexyl, heptyl, cyclopentyl, cyclohexyl, cyclohexylmethyl and the like.

The term alkoxy refers to straight or branched chain oxyalkyl groups such as, e.g., methoxy, ethoxy, butoxy, heptoxy, dodecyloxy, and the like.

Pharmaceutically acceptable salts suitable as acid addition salts are those from acids such as hydrochloric, hydrobromic, phosphoric, sulfuric, maleic, citric, acetic, tartaric, succinic, oxalic, malic, glutamic and the like, and include other acids related to the pharmaceutically acceptable salts listed in *Journal of Pharmaceutical Science*, 66:2 (1977).

Generally, the process of the invention comprises the following steps a) nitration of compound 2 of the formula

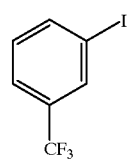

to afford compound 3 of the formula

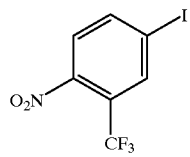
3 b) reaction of compound 3 with trifluoromethyl copper to afford compound 4 of the formula

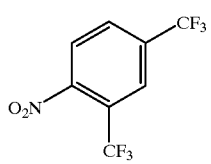
4 c) displacement of the nitro of compound 4 with dimethyl malonate to afford compound 5 of the formula

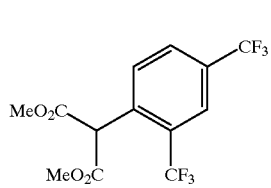
5 d) which is subsequently hydrolyzed and decarboxylated to afford compound 6, the 2,4-bis(trifluoromethyl) phenylacetic acid side chain of the formula,

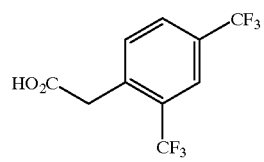
6

The side chain is attached to the benzodiazepine nucleus of Compound 1 as shown below.

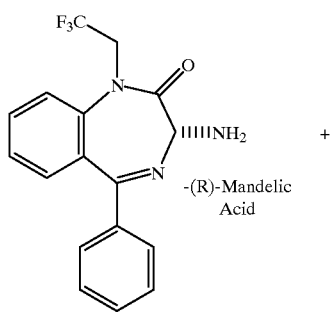

+ -(R)-Mandelic Acid

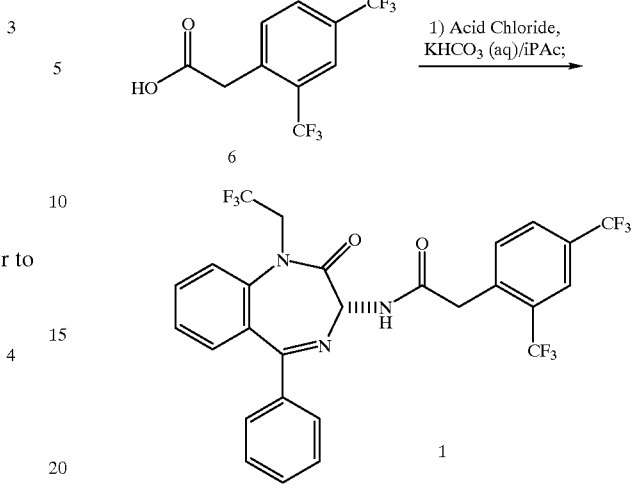

The invention is illustrated in the following steps wherein preferred reactants are shown to more clearly demonstrate the process disclosed.

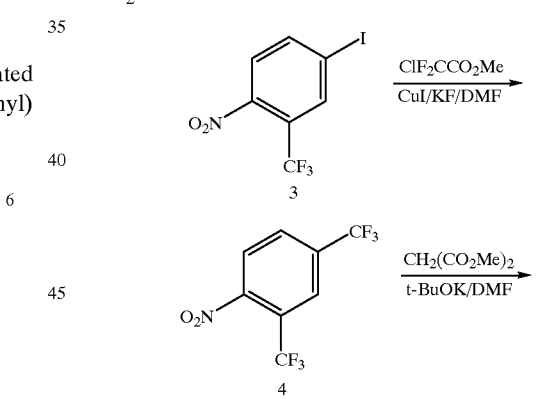

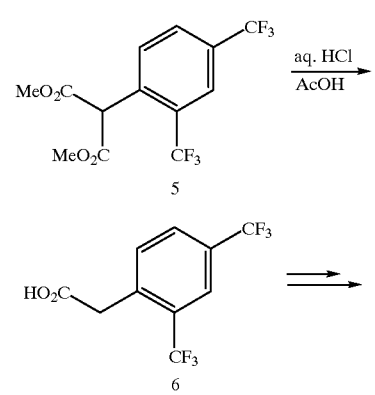

-continued

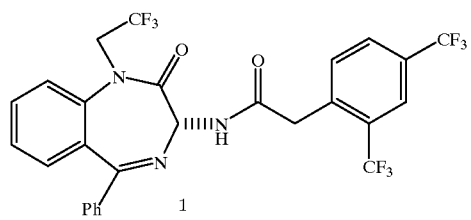

As shown above, Step 1 involves the nitration of commercially available starting material 3-iodobenzotrifluoride in nitric or other suitable acids. The reaction takes place at a temperature range of about 0° C. to about 80° C. over 0.5 to 5 hours. Preferred conditions include a temperature range of about 20° C. to about 35° C. over 2 to 3 hours. Particularly preferred conditions are 20° C. for 2 hours.

A hexane wash following the nitration step is critical to remove unwanted regioisomers.

Step 2 involves the trifluoromethylation of Compound 3 as described in Chen et al., Tet. Lett., 1991, 7689. Iodobenzene compound 3 is reacted with methyl chlorodifluoroacetate with copper iodide in the presence of potassium fluoride. DMF or other suitable solvent such as n-methyl pyrrolidinone or n-ethyl pyrrolidinone can be used The reaction takes place at a temperature range of about 90° C. to about 130° C. over 1 to 10 hours. Preferred conditions include a temperature of about 103° C. for 4 hours.

In Step 3 the nitro substituent on compound 4 is displaced by reaction with dimethyl malonate to provide compound 5, the dimethyl ester. The reaction could use any alkyl malonate to prepare any alkyl ester. However, the dimethyl malonate is preferred. The reaction takes place in the presence of potassium butoxide or other suitable base. DMF or other suitable solvents such as n-methyl pyrrolidinone can be used. The displacement reaction takes place at a temperature range of about −10° C. to about 75° C. over 1 to 48 hours. Preferably, the displacement reaction takes place at a temperature range of about 15° C. to about 30° C. over 20 to 30 hours.

The hydrolysis and decarboxylation of Compound 5 is accomplished using an acid such as aqueous HCl in acetic acid. This reaction takes place at a temperature range of about 75° C. to about 150° C. over 1 to 24 hours. Preferably, the reaction takes two hours at 100° C. to give the side chain in high assay yield.

Following the synthesis of the side chain, it is can be coupled, as described above, to prepare Compound 1.

The invention is described in greater detail in the following examples in which all parts, preparations, ratios and percentages are by weight unless otherwise indicated. These are for illustrative purposes and are not to be construed as limiting the invention described and claimed herein. All temperatures are given in degrees centigrade (°C.) unless otherwise noted.

EXAMPLE 1

(1) Nitration

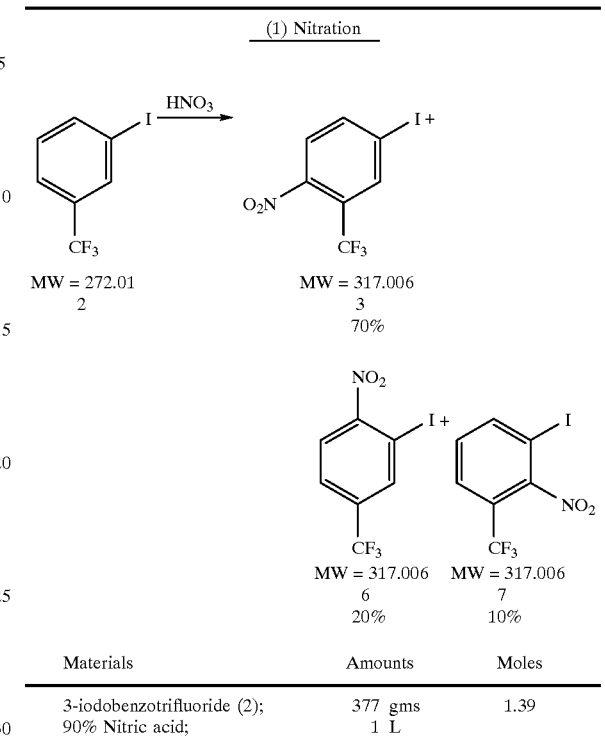

| Materials | Amounts | Moles |
|---|---|---|
| 3-iodobenzotrifluoride (2); | 377 gms | 1.39 |
| 90% Nitric acid; | 1 L | |

To a 4-neck 22 L round bottom flask with a mechanical stirrer, thermocouple, heating mantle and $N_2$ inlet containing 90% nitric acid was added 3-iodobenzotrifluoride (2) over 15 minutes at 20° C. A mild exotherm was observed. The reaction mixture was stirred at 20 ° C. for two hours after which time no 3-iodobenzotrifluoride (2) was observed by LC. The reaction mixture was slowly added to 1L ice water. The slurry was stirred for 30 minutes and filtered. The solids were washed with hexanes (2×150 ml). 240 grams (55%) of solid was obtained and used directly in the next step.

The hexane wash removed the undesired isomer 7 as well as 6 and about 10% of the desired 3. The conversion of 2 to products was monitored by LC by adding ~5 ul of the reaction mixture to 1.5 ml $CH_3CN$. The LC conditions: Zorbax Rx-C8, 4.6×250 mm, 65:35 =$CH_3CN:H_2O$ (0.1% $H_3PO_4$), Flow rate=1.0 ml/min., at 220 nm, Rt =8.3 min (for 2); 7.6 min (for 3).

EXAMPLE 2

(2) Trifluoromethylation

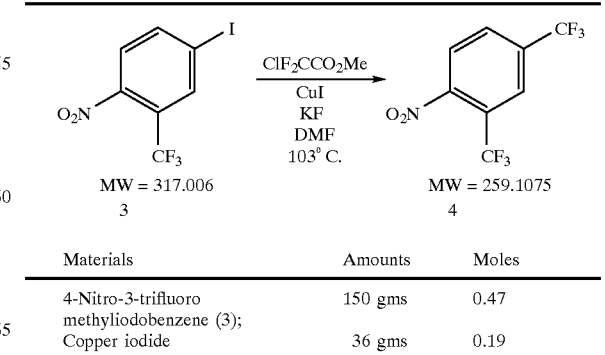

| Materials | Amounts | Moles |
|---|---|---|
| 4-Nitro-3-trifluoro methyliodobenzene (3); | 150 gms | 0.47 |
| Copper iodide | 36 gms | 0.19 |

-continued

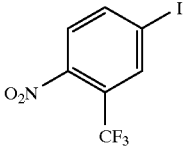

| Materials | Amounts | Moles |
|---|---|---|
| Methylchlorodifluoroacetate | 205 gms | 1.42 |
| Potassium fluoride | 55 gms | 0.95 |
| Dimethylformamide | 750 ml | |

To a 3-neck 2 L round bottom flask with a mechanical stirrer, thermocouple, heating mantle, condenser, addition funnel and $N_2$ inlet was charged 4-nitro-3-trifluoromethyliodobenzene (3) and DMF. 50 grams methyl chlorodifluoroacetate, copper iodide and potassium fluoride were added and the reaction mixture was heated to 103° C. The remaining methyl chlorodifluoroacetate was added via addition funnel over 1 hour. After four hours at 103° C. all starting material was consumed. The reaction solution was cooled to room temperature and poured into 1L $H_2O$/50 ml $NH_4OH$. Extracted with EtOAc (2×400 ml) and the combined organics were washed with water (3×500 ml). The organics were evaporated and flushed with EtOAc (3 ×250 ml) to remove water. The crude oil was assayed (85.3 g of 4, 70% yield) and used directly in the next step.

EXAMPLE 3
(3) Nitro-displacement

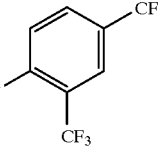

| Materials | Amounts | Moles |
|---|---|---|
| Bis(trifluoromethyl)nitro benzene 4 | 20.4 gms | 0.08 |
| Dimethyl malonate | 31.3 gms | 0.24 |
| Potassium t-butoxide | 26.6 gms | 0.24 |
| Dimethylformamide | 183 ml | |

To a 3-neck 1 L round bottom flask with a mechanical stirrer, thermocouple, cooling bath, addition funnel and $N_2$ inlet was charged dimethyl malonate and DMF. The solution was cooled to 15° C. Potassium t-butoxide was added over 15 minutes as a solid. A solution of Bis(trifluoromethyl) nitrobenzene 4 (in 20 ml of DMF) was added via addition funnel over 10 minutes. The reaction mixture was warmed to room temperature and aged overnight. LC assay showed consumption of 4 and the reaction was quenched into 500 ml water. The quenched solution was extracted with EtOAc (2×400 ml) and the combined organics washed with water (3×500 ml). The resulting solution was assayed (18.8 g of 5, 70% yield) and solvent switched to AcOH for use in the next step.

EXAMPLE 4
(4) Hydrolysis/Decarboxylation

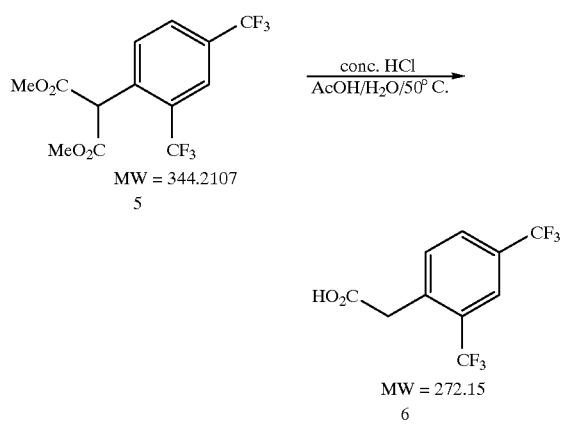

| Materials | Amounts | mmol |
|---|---|---|
| Dimethylester 5 | 10.0 g | 29.1 |
| Acetic Acid | 50 ml | |
| HCl (conc) | 10 ml | |
| Water | 5 ml | |
| Hexane | 30 ml | |

To a 3-neck 250 ml round bottom flask with a mechanical stirrer, thermocouple, heating mantle and $N_2$ inlet was charged dimethyl ester 5 with acetic acid, conc. HCl and water. The resulting solution was heated to 100° C. for six hours. LC assay indicated that 5 had been consumed and the reaction was quenched into 100 ml water. The quenched solution was extracted with EtOAc (2×100 ml) and the combined organics washed with water (3×100 ml). The resulting solution was assayed and solvent switched to hexane (30 ml). The slurry was heated to 50° C. to dissolve all solids. The solution was slowly cooled to 20° C. The slurry was filtered and washed with hexane (3 ml). The solids were dried and 4.7 grams (60%) of a solid were obtained. The mother liquors contained 10% of the phenylacetic acid 6.

EXAMPLE 5

(4) Coupling

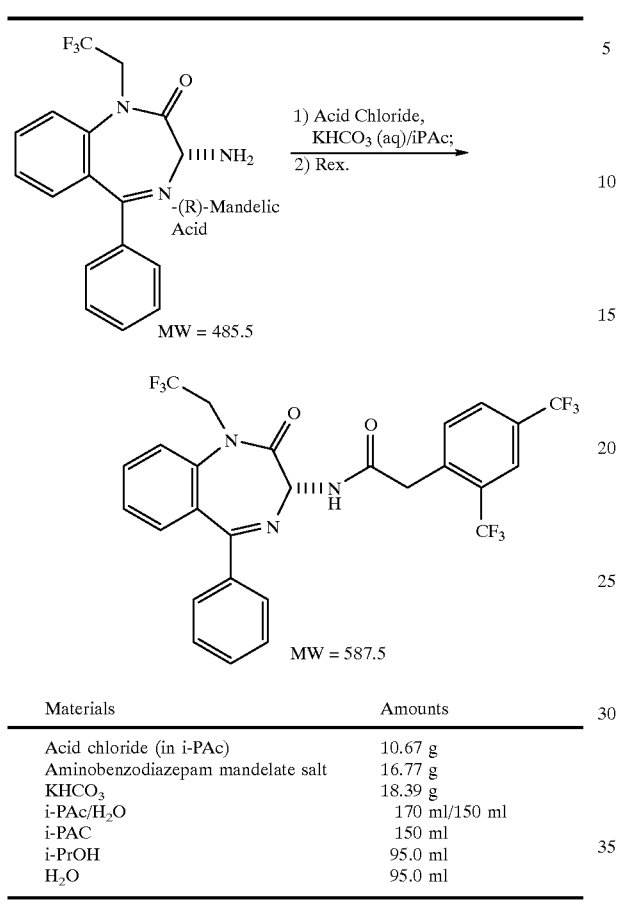

| Materials | Amounts |
| --- | --- |
| Acid chloride (in i-PAc) | 10.67 g |
| Aminobenzodiazepam mandelate salt | 16.77 g |
| KHCO₃ | 18.39 g |
| i-PAc/H₂O | 170 ml/150 ml |
| i-PAC | 150 ml |
| i-PrOH | 95.0 ml |
| H₂O | 95.0 ml |

The mandelate salt (10 ml/g) was charged into the reaction vessel, followed by addition of i-PAc and aqueous KHCO₃ [KHCO₃ (18.4 gms)/water (150 ml)] at 20° C. The slurry was stirred at 20–22° C. for 5–10 min followed by addition of the acid chloride solution (ca. 25 ml) over 15 min. at 20–22° C. (a slight exotherm was observed). The mixture was stirred at 22° C. for one hour and LC assay showed the completion of the reaction. The layers was separated and the organic layer was washed with 50% saturated NaHCO₃ (100 ml×3) and with water (100 ml×2).

The crude product was recrystallized from i-PrOH/H₂O to afford Compound 1.

What is claimed is:

1. A process for the synthesis of the compound of the formula

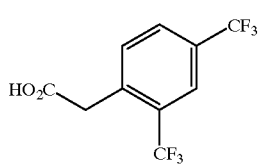

which comprises the steps of a) nitration of compound 2 of the formula

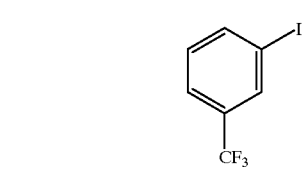

to afford compound 3 of the formula

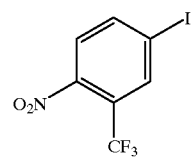

b) reaction of compound 3 with trifluoromethyl copper to afford compound 4 of the formula

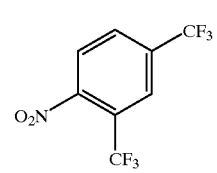

c) displacement of the nitro of compound 4 to afford compound 5 of the formula

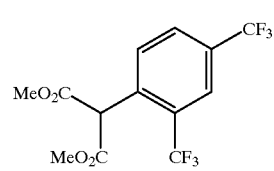

d) which is subsequently hydrolyzed and decarboxylated to afford compound 6.

2. The process of claim 1 wherein the nitro displacement in Step (c) is accomplished using dimethyl malonate.

3. The process of claim 2 wherein the displacement reaction takes place at a temperature of about 15° C. to about 30° C. over 20 to 30 hours.

4. The process of claim 1 wherein following the nitration of compound 2, the reaction mixture undergoes a hexane wash in order to remove unwanted regioisomers of compound 3.

* * * * *